(12) United States Patent
Machida et al.

(10) Patent No.: US 6,632,939 B2
(45) Date of Patent: Oct. 14, 2003

(54) PROCESS FOR PRODUCING DEXTRAN REDUCED IN BORON CONTENT

(75) Inventors: Haruo Machida, Hino (JP); Shigeaki Kato, Hachioji (JP); Yuuki Hirata, Naruto (JP); Mitsuo Aoki, Naruto (JP); Hideki Kobatake, Naruto (JP)

(73) Assignees: Meito Sangyo Co., Ltd., Aichi (JP); Otsuka Pharamaceutical Factory, Inc., Tokushima (JP)

( * ) Notice: Subject to any disclaimer, the term of this patent is extended or adjusted under 35 U.S.C. 154(b) by 0 days.

(21) Appl. No.: 09/529,097

(22) PCT Filed: Oct. 7, 1998

(86) PCT No.: PCT/JP98/04541

§ 371 (c)(1),
(2), (4) Date: Apr. 7, 2000

(87) PCT Pub. No.: WO99/19364

PCT Pub. Date: Apr. 22, 1999

(65) Prior Publication Data

US 2003/0018010 A1 Jan. 23, 2003

(30) Foreign Application Priority Data

Oct. 9, 1997 (JP) .............................................. 9-277787
Jun. 25, 1998 (JP) ........................................... 10-179096

(51) Int. Cl.⁷ ............................................... C08B 37/02
(52) U.S. Cl. ...................................... 536/112; 536/127
(58) Field of Search ................................. 536/112, 127

(56) References Cited

U.S. PATENT DOCUMENTS

| 2,644,815 A | * | 7/1953 | Gronwall et al. | ............ 260/209 |
| 4,208,392 A | | 6/1980 | Allain et al. | ................ 423/497 |
| 5,484,715 A | * | 1/1996 | Kado et al. | .................. 435/103 |

FOREIGN PATENT DOCUMENTS

| EP | 673103 | 6/1952 |
| JP | 54-113488 | 9/1979 |
| JP | 59-20301 | 2/1984 |
| JP | 09-239000 | 9/1997 |

* cited by examiner

Primary Examiner—Kathleen K. Fonda
Assistant Examiner—Leigh C. Maier
(74) Attorney, Agent, or Firm—Finnegan, Henderson, Farabow, Garrett & Dunner LLP

(57) ABSTRACT

The present invention relates to dextran whose boron content is reduced to a value less than 0.30 $\mu$g/g (dry basis) calculated on the basis of boron atom, a process for producing the same, and dextran with which a container is filled in a solution state. Dextran of the present invention is obtained by treating a boron-containing dextran with a lower alcohol, and said dextran has such a characteristic that deposition is inhibited or the deposition rate is drastically reduced when using it in the form of a solution. Therefore, an isotonic sodium chloride solution of said dextran is suitably used as substitute plasma or external perfusate in an operation.

4 Claims, 2 Drawing Sheets

14···MOLECULAR CHAIN OF DEXTRAN
15···BORON

# PROCESS FOR PRODUCING DEXTRAN REDUCED IN BORON CONTENT

TECHNICAL FIELD

The present invention relates to dextran whose boron content is reduced, a process for producing the same, and dextran with which a container is filled in a solution state.

BACKGROUND ART

Dextrans are polysaccharides produced by fermentation of sucrose using bacteria capable of producing dextran (e.g. *Leuconostoc mesenteroides, Leuconostoc dextranicum*, etc.). Those having a proper molecular weight among produced dextrans have hitherto been used as substitute plasma in a treatment on acute bleeding, preventive and remedy for surgical shock due to injury or bleeding, or external perfusate in an operation, after being dissolved in an isotonic sodium chloride solution. A complex with iron as a derivative of dextran is used as an injection to iron-deficiency anemia. A sulfate ester of dextran is used as a blood coagulant in place of heparin. Also, dextrans have been used in various industrial fields such as food industry.

Dextran is generally produced through production processes as shown in FIG. 2. First, sucrose as a raw material and an inorganic salt such as dipotassium phosphate are charged in a raw material dissolution vessel 1, together with vitamins and water, and then dissolved. The raw material solution is supplied to a fermentation vessel 2, where the solution is fermented by adding bacteria capable of producing dextran. After the completion of fermentation, the fermented solution is supplied to a precipitation vessel 3, where dextran is precipitated by adding methanol and then separated.

In a hydrolysis vessel 4, hydrolysis is conducted by adding hydrochloric acid, and then impurities are removed by using a filter 5. A dextran section, which is precipitated at a fixed methanol concentration, is collected in a fractional precipitation vessel 6 and, after dissolving the dextran section in a dissolution vessel 7, salts are removed in an ion exchange column 8. Dextran is dissolved again in a dissolution vessel 9, and then supplied to a spray dryer 13 via a filter 10, an evaporator 11 and a control tank 12, followed by spray drying to obtain a dextran powder.

The dextran powder thus obtained is used as an injection in the medical field, after it was dissolved in an isotonic sodium chloride solution and a container is filled with it and then sealed, as described above. However, when dextrin obtained by a conventional process is dissolved and a container is filled with the resulting solution, there arises a problem that a crystal of dextran is liable to be deposited as a result of a change in temperature during the storage or transportation.

When using a dextran solution as substitute plasma or external perfusate, it is necessary that a crystal of dextran is not deposited in the dextran solution.

However, since it is difficult to dissolve once deposited crytal of dextran again even when using means such as heating or shaking, an injection container filled with a dextran solution containing a deposited crystal must be discarded.

It is, therefore, an object of the present invention to provide dextran which hardly causes deposition of a crystal even when using in the form of a solution, a process for producing the same, and dextran with which a container is filled in a solution state.

DISCLOSURE OF THE INVENTION

The present inventors have studied intensively to solve the above problems and studied furthermore on the assumption that impurities contained in dextran produced by a conventional process exert an influence on deposition of a crystal of dextran. As a result, they have obtained such a novel finding that boron contained in dextran has a function of accelerating deposition of dextarn, surprisingly.

On the basis of such a finding, the present inventors have studied furthermore and found a fact that deposition of a crystal from a dextran solution is inhibited or drastically reduced by controlling the content of boron in dextran to a value less than 0.30 $\mu$g/g (dry basis) calculated on the basis of boron atom. Thus, the present invention has been completed.

That is, the present invention includes the following inventions:

(1) Dextran whose boron content is reduced, said boron content being less than 0.30 $\mu$g/g (dry basis) calculated on the basis of boron atom;

(2) Dextran according to the term (1), wherein said boron content is not more than 0.20 $\mu$g/g (dry basis) calculated on the basis of boron atom;

(3) Dextran according to the term (1) or (2), with which a container is filled in a solution state;

(4) Process for producing dextran whose boron content is reduced, which comprises treating a boron-containing dextran with a lower alcohol, thereby to reduce the boron content to a value less than 0.30 $\mu$g/g (dry basis) calculated on the basis of boron atom; and (5) The process according to the term (4), wherein said boron-containing dextran as a starting material is in the form of a powder or an aqueous solution and is treated with a lower alcohol.

The term "boron content" used in the present invention refers to a value ($\mu$g) wherein an amount of boron based on a dry weight (g) of dextran contained in a powder or solution of dextran of the present invention is represented by calculation on the basis of boron atom.

DESCRIPTION OF REFERENCE NUMERALS

1: raw material dissolution vessel, 2: fermentation vessel, 3: precipitation vessel, 4: hydrolysis vessel, 5: filter, 6: fractional precipitation vessel, 7: dissolution vessel, 8: ion exchange column, 9: dissolution vessel, 10: filter, 11: evaporator, 12: control tank, 13: spray dryer, 14: molecular chain of dextran, 15: boron

BEST MODE FOR CARRYING OUT THE INVENTION

Dextran of the present invention is obtained by treating a boron-containing dextran as a raw material with a lower alcohol. It can be produced by dissolving boron-containing dextran as a raw material for dextran in a lower alcohol and optionally drying the solution.

That is, the process for producing dextran according to the present invention is characterized by treating a boron-containing dextran with a lower alcohol, thereby to reduce the boron content to a value less than 0.30 μg/g (dry basis) calculated on the basis of boron atom.

The boron-containing dextran as a starting material may be in the form of a powder or an aqueous solution.

Regarding dextran of the present invention, deposition of a dextran crystal is inhibited or its deposition rate is drastically reduced as described above. Therefore, the solution prepared by dissolving dextran can be effectively used for practical use after a container such as container of dextran injection is filled with it.

In the present invention, boron contained in dextran as the raw material also includes any form of boron atom or a compound containing boron atom.

Contamination of dextran with boron is caused by various factors, for examples, leakage of boron from a device or a container on production of dextran, and contamination with boron from a fermentation medium capable of producing dextran.

It is considered that boron is leaked out in a dextran solution in case where a dextran solution is brought into contact with a wall surface of containers or devices, such as raw material dissolution vessel 1, fermentation vessel 2, precipitation vessel 3, and filter medium used in filters 5 and 10, particularly wall surface made of glass. Boron is contained in the medium as a trace element, sometimes, thereby making it impossible to avoid contamination of dextran as a fermentation product with boron.

The boron content of dextran thus produced is usually within a range from about 0.30 to 1.20 μg/g (dry basis) calculated on the basis of boron atom.

Figure 2:
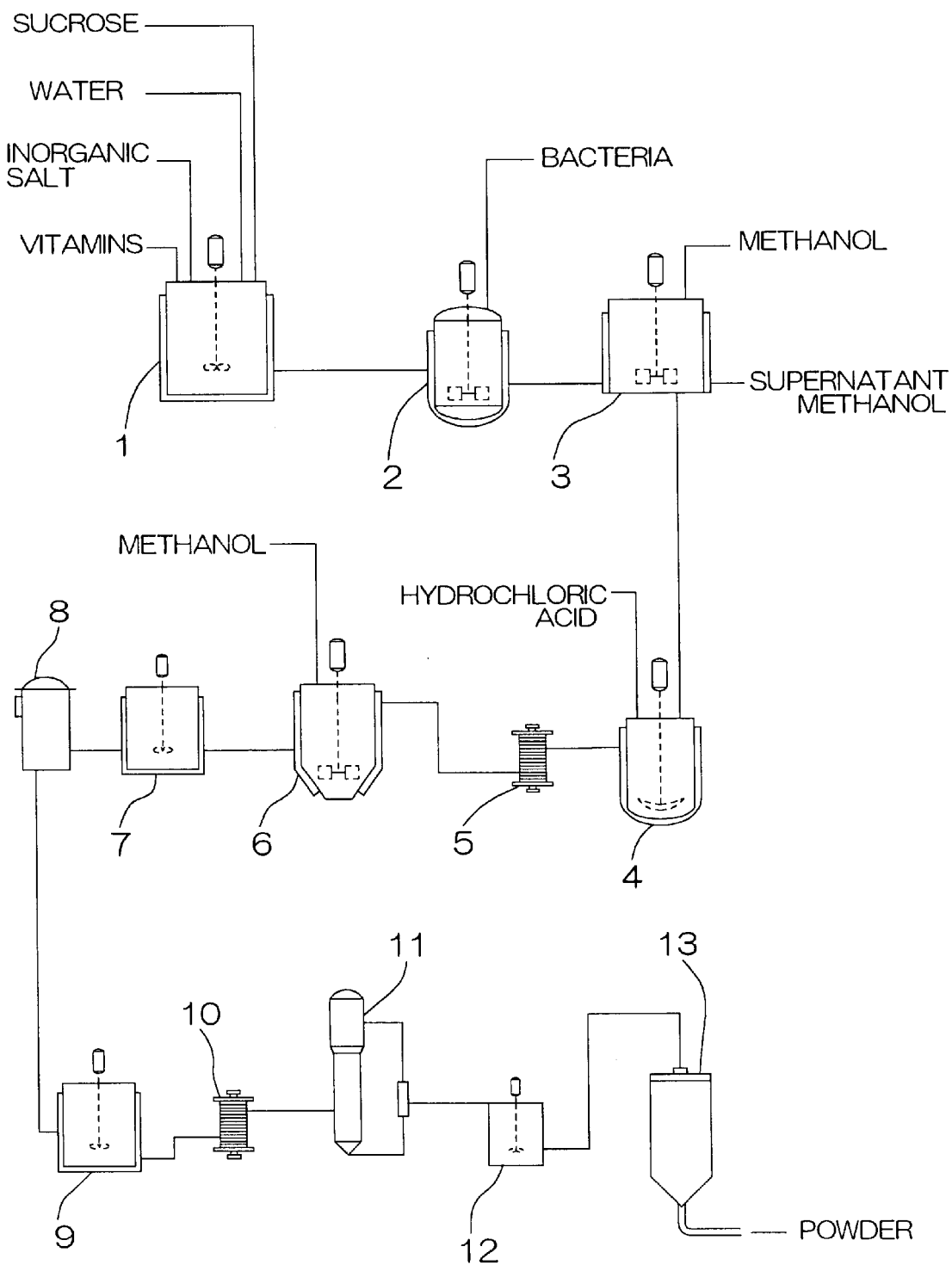
FIG. 2 is a flow sheet showing a production process of dextran.

Although methanol is used to conduct fractional precipitation of dextran in the production process shown in FIG. 2, it is impossible to obtain dextran of the present invention, i.e. dextran whose boron content is less than 0.30 μg/g (dry basis) calculated on the basis of boron atom, by a treatment with methanol in this production process.

The process for producing dextran of the present invention will be described below.

The present process is characterized by treating a boron-containing dextran with a lower alcohol. More specifically, the present process is characterized by bringing boron-containing dextran into contact with a lower alcohol, thereby to convert boron into a trialkyl borate, and separating the trialkyl borate from dextran to obtain dextran whose boron content after the treatment is less than 0.30 μg/g (dry basis) calculated on the basis of boron atom.

The lower alcohol used herein is preferably a lower alcohol wherein the number of carbon atoms of an alkyl group is from about 1 to 4. Among these lower alcohols, methanol or ethanol is particularly preferred. The boron-containing dextran used as the raw material may be in the form of a powder, or may be those dispersed or dissolved in water.

Removal of boron from the dextran powder (raw material) containing boron may be conducted by dispersing the dextran powder into a lower alcohol, thereby to convert boron into a trialkyl borate represented by the following formula:

$$B(OR)_3$$

(wherein R represents a lower alkyl group having 1 to 4 carbon atoms), separating dextran from the lower alcohol by filtration, and drying. Whereby boron contained in the dextran powder is dissolved in the lower alcohol to form a trialkyl borate, which is then separated from dextran.

Washing of the dextran powder with the lower alcohol may be once conducted, but is preferably repeated plural times so as to reduce to the desired boron content (to a value less than 0.30 μg/g (dextran dry basis) calculated on the basis of boron atom). The amount of the lower alcohol used is not specifically limited as far as it is an excess amount based on dextran. Dissolution of the dextran powder into the lower alcohol may be conducted at room temperature with stirring, or conducted with warming or heating appropriately.

An aqueous solution of dextran may be to be used in place of a dextran powder. In this case, the treatment may be conducted in the same manner as described above, except for adding a lower alcohol to an aqueous dextran solution. In that case, the concentration of dextran in the aqueous solution is preferably controlled within a range from about 20 to 30% by weight. The amount of the lower alcohol to be added is controlled within a range from ½ to ⅓ in a volume ratio based on the aqueous dextran solution.

By using the above process, the content of boron in dextran is reduced to a value less than 0.30 μg/g (dry basis), preferably not more than 0.25 μg/g, and more preferably not more than 0.20 μg/g, calculated on the basis of boron atom. When using as an injection, the boron content is reduced to 0.20 μg/g or less calculated on the basis of boron atom, particularly preferably.

This dextran powder can be used as a dextran solution such as injection after it was dissolved in purified water, together with the other components, and a container such as plastic bag or glass vial is filled with the resulting solution, sealed, and then sterilized with heating. In this case, the concentration of dextran is generally from about 3 to 10% by weight.

Figure 1:
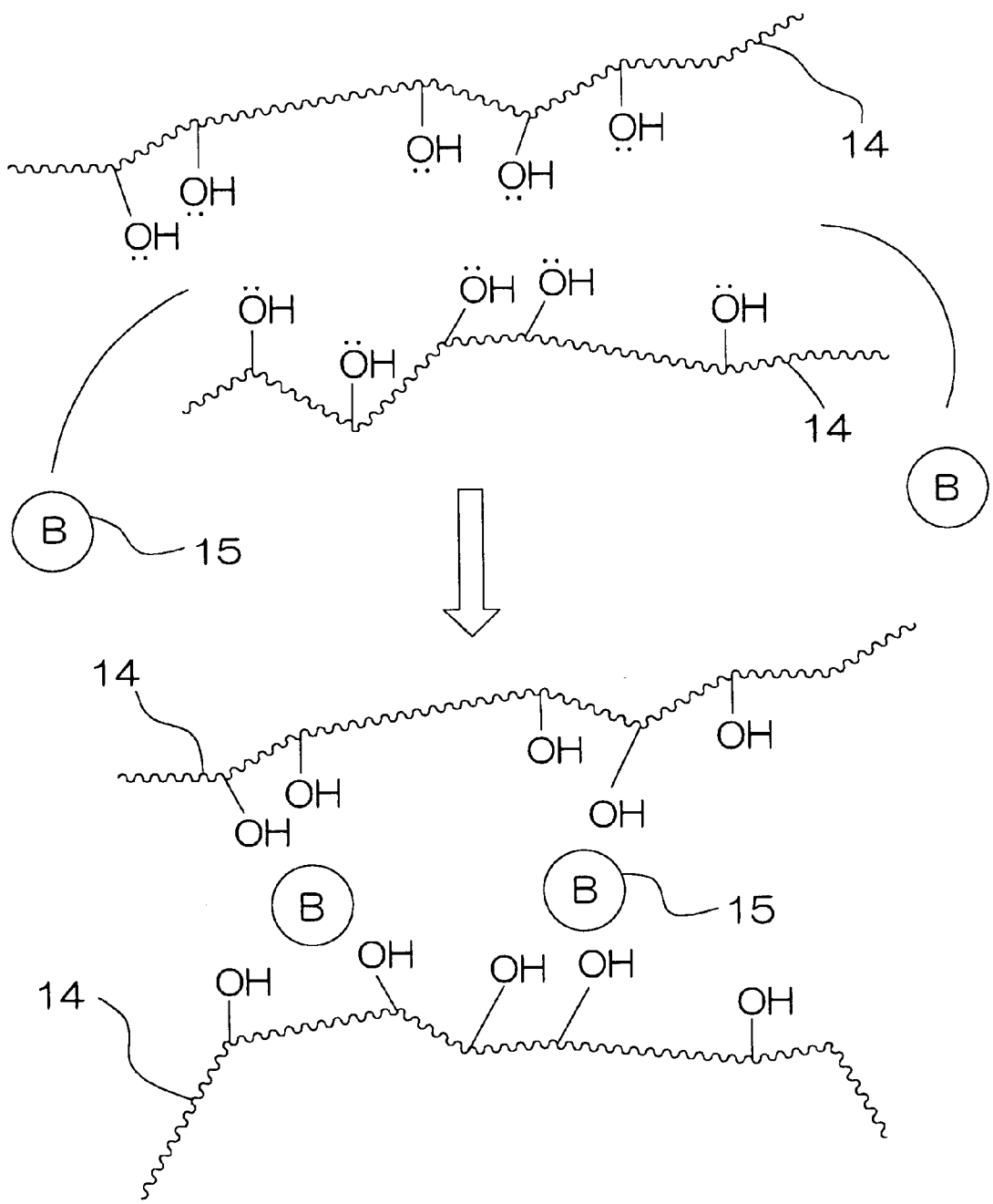
FIG. 1 is a schematic diagram showing an action of boron to dextran.

Dextran whose boron content was reduced, with which a container is filled in a solution state, in the present invention makes it possible to inhibit a dextran crystal from depositing on an inner wall of a vessel during the storage or transportation due to a change in temperature, or to drastically reduce the deposition rate. A theoretical relation between the deposition of the dextran crystal and boron is not clear, necessarily. However, it is assumed that a molecular chain 14 of dextran forms a crosslinked structure via boron 15 on the basis of a pair of non-covalent electrons in hydroxyl groups of the molecular chain 14 as is schematically shown in FIG. 1 and, as a result, dextran is liable to be deposited. It is considered, the content of boron in dextran is reduced as described above according to the present invention and, therefore, deposition of dextran is inhibited or the deposition rate is drastically inhibited.

EXAMPLES

The following Examples and Test Examples further illustrate the present invention in detail.

Example 1

200 g of a dextran powder (manufactured by Meito Sangyo Co., Ltd., number-average molecular weight: 40,000, glucan obtained by α-1,6-bond) was dissolved in 1000 ml of water and 300 ml of methanol was added to the solution, followed by stirring at room temperature for 10 minutes. After stirring, the treated solution was dried under reduced pressure.

Each content of boron in the dextran powder before and after treating with methanol was measured in the following manner (repeated number n=2).
(Measuring Procedure)

0.04 g of a sample was dissolved in ultrapure water and, after adding 0.04 ml of nitric acid, 4 ml of a solution was prepared by using ultrapure water. The boron content of this solution was measured by using an ICP mass spectrometer ("Model SPQ9000", manufactured by Seiko Denshi Kogyo Co., Ltd.).

The results are shown in Table 1.

TABLE 1

| Samples | Boron content (µg/g) | | |
|---|---|---|---|
| | 1 | 2 | average |
| Before treatment | 0.28 | 0.31 | 0.30 |
| After treatment | 0.16 | 0.14 | 0.15 |

As is apparent from the results shown in Table 1, the boron content is drastically reduced by a treatment with methanol.

Example 2

In the same manner as in Example 1, except that 200 g of a dextran powder was added to 200 ml of methanol, a dextran powder treated with methanol was obtained.

Dextran of the present invention was formed into a preparation (injection), the following respective tests were conducted.

Test Example 1

Dextran treated with methanol in the same manner as in Example 1 was dissolved in ultrapure water to prepare an aqueous 10 w/v % dextran solution. Then, a 100 ml glass vial was filled with 50 ml of the dextran solution and sealed to make a dextran solution with which a container is filled (sample 1).

Using dextran before treating with methanol (manufactured by Meito Sangyo Co., Ltd., dextran having a number-average molecular weight of 40,000), a dextran solution with which a container is filled (sample 2) was made in the same manner as described above.

Each of the resulting samples (n=5) was allowed to stand sunny outdoors (average temperature: about 28° C.) and it was visually observed whether precipitation of a dextran crystal occurs or not after 1 and 4 days had passed since the beginning of the test. The results are shown in Table 2.

In the table, a denominator of a fraction denotes the number of samples tested, whereas, a numerator of a fraction denotes the number of samples where precipitation occurred.

TABLE 2

| | Frequency of occurrence of dextran deposition | |
|---|---|---|
| Samples | After 1 day | after 4 days |
| 1 | 0/5 | 0/5 |
| 2 | 2/5 | 4/5 |

As is apparent from the results shown in Table 2, precipitation of dextran occurred after one day since the beginning of the test in the sample 2 using dextran whose boron content was not reduced under severe storage conditions with direct sunlight at high temperature.

In the sample 1 using dextran whose boron content was reduced by a treatment with methanol, precipitation of dextran was not recognized in all test samples.

Test Example 2

With respect to the sample 2 used in Test Example 1, trace elements contained in the original dextran powder as a starting material and those contained in the precipitate were analyzed, respectively.

After dissolving the samples in nitric acid, the respective trace elements were measured by using the ICP mass spectrometer (aforementioned) in the same manner as in the analysis procedure of Example 1. Calcium was measured by a graphite crucible heating-atomic absorption spectrometry. The measurement results are shown in Table 3.

TABLE 3

| | Original dextran powder | Precipitate |
|---|---|---|
| Boron | + | +++ |
| Aluminum | + | + |
| Calcium | ++ | ++ |
| Magnesium | + | + |

+: 0.1 to 1 µg/g
++: 1 to 10 µg/g
+++: 10 to 100 µg/g

As is apparent from the results shown in Table 3, each content of elements such as aluminum, calcium and magnesium in the original dextran powder is almost the same as that in the precipitate, whereas, the content of boron in the precipitate was 10 or more time larger than that in the dextran powder. As is apparent from these results, the presence of boron takes part in deposition of dextran.

Test Example 3

As is apparent from the results of the above Test Examples, a container filled with a dextran solution made from a dextran powder whose boron content was reduced (sample 1) caused less rejects than a container filled with a dextran solution made from a dextran powder whose boron content was not reduced at all (sample 2, conventional product).

The present inventors have studied how much the content of boron in dextran must be actually reduced in order to reduce occurrence of deposition in a container filled with a solution of dextran and to effectively prevent occurrence of rejects.

As the test procedure, the following quantitative test was conducted to examine the frequency of occurrence of rejects to the content of boron in the dextran solution.

Assuming the case where the above container filled with dextran is commercialized, the temperature close to the storage condition of a pharmaceutical preparation (average temperature: 22° C.) was selected as the storage condition.

(Production of Sample)

Dextran treated with methanol in the same manner as in Test Example 1 was dissolved in ultrapure water to prepare an aqueous 10 w/v % dextran solution. Then, 200 ml of this solution was respectively charged in eight plastic containers and each aqueous boric acid solution (80.08 ppm) was added in the amount of 0.29 ml, 0.36 ml, 0.39 ml, 0.42 ml, 0.43 ml, or 0.50 ml. The content of boron in each plastic container is 0.20 ppm, 0.25 ppm, 0.275 ppm, 0.295 ppm, 0.30 ppm, or 0.35 ppm based on the weight (dry basis) of dextran in which boron is dissolved.

After 20 ml of the solution was taken out from each container, a 100 ml polyethylene bag was filled with it and then sealed to make a container filled with the dextran solution.

Using a dextran powder (manufactured by Meito Sangyo Co., Ltd., dextran having a number-average molecular weight of 40,000, conventional product), a container filled with the dextran solution, as a control, was made in the same manner as described above. The content of boron in the container as a control is 1.20 ppm based on the weight (dry basis) of dextran in which boron is dissolved.

(Test Procedure)

Each of the resulting samples (n=5) was allowed to stand sunny outdoors (average temperature: about 22° C.) and it was visually observed whether precipitation of a dextran crystal occurs or not after 1 day, 4 days, 6 days, 10 days and 21 days had passed since the beginning of the test. The results are shown in Table 4. In the table, a denominator of a fraction denotes the number of samples tested, whereas, a numerator of a fraction denotes the number of samples where precipitation occurred.

TABLE 4

| Concentration of boron (ppm) | Frequency of occurrence of dextran deposition | | | | |
|---|---|---|---|---|---|
| | after 1 day | after 4 days | after 6 days | after 10 days | after 21 days |
| 0.200 | 1/5 | 1/5 | 3/5 | 3/5 | 3/5 |
| 0.250 | 0/5 | 0/5 | 3/5 | 3/5 | 3/5 |
| 0.275 | 0/5 | 0/5 | 2/5 | 2/5 | 2/5 |
| 0.295 | 0/5 | 0/5 | 2/5 | 2/5 | 2/5 |
| 0.300 | 1/5 | 2/5 | 5/5 | — | — |
| 0.350 | 1/5 | 2/5 | 5/5 | — | — |
| Control | 3/5 | 4/5 | 5/5 | — | — |

As is apparent from the results shown in Table 4, occurrence of deposition is inhibited even after 21 days have passed since the beginning of the test in case the boron content is less than 0.30 ppm based on the weight (dry basis) of dextran in which boron is dissolved.

INDUSTRIAL APPLICABILITY

According to dextran of the present invention, deposition after dissolution is inhibited or the deposition rate is drastically reduced and, therefore, frequency of occurrence of rejects due to dextran deposition can be inhibited or reduced until it is used after sealing in a container. For example, an isotonic sodium chloride solution of dextran according to the present invention is suited for medical use such as substitute plasma or external perfusate.

What is claimed is:

1. A process for producing dextran having a reduced boron content which comprises preparing a solution obtained by contacting a boron-containing dextran as a starting material with a lower alcohol to convert boron in the dextran into a trialkyl borate and; separating the trialkyl borate from the dextran, so that the boron content of the dextran starting material is reduced to a value of not more than 0.20 $\mu$g/g (dry basis) calculated on the basis of boron atom.

2. The process according to claim 1, wherein said boron-containing dextran starting material is in the form of a powder or an aqueous solution.

3. The process according to claim 2, wherein the starting material is an aqueous solution in which the concentration of dextran in the aqueous solution is controlled within a range from about 20 to 30% by weight and the amount of the lower alkyl is controlled within a range from ½ to ⅓ in a volume ratio based on the aqueous dextran solution.

4. The process of claim 1, wherein the lower alcohol is methanol or ethanol.

* * * * *